US00PP13861P29

(12) United States Plant Patent
Holtrop

(10) Patent No.: US PP13,861 P2
(45) Date of Patent: Jun. 3, 2003

(54) SNAPDRAGON PLANT NAMED 'DRAYEL'

(75) Inventor: Mathilde H. Holtrop, Aromas, CA (US)

(73) Assignee: Goldsmith Seeds Inc., Gilroy, CA (US)

( * ) Notice: Subject to any disclaimer, the term of this patent is extended or adjusted under 35 U.S.C. 154(b) by 0 days.

(21) Appl. No.: 10/059,365

(22) Filed: Jan. 31, 2002

(51) Int. Cl.[7] ..... A01H 5/00
(52) U.S. Cl. ..... Plt./322
(58) Field of Search ..... Plt./322

*Primary Examiner*—Kent Bell
(74) *Attorney, Agent, or Firm*—Jondle & Associates PC

(57) ABSTRACT

A snapdragon cultivar particularly distinguished by yellow flowers, vigorous growth and basal branching.

1 Drawing Sheet

Genus and Species: *Antirrhinum hybrida.*
Variety Denomination: 'Drayel'.

BACKGROUND OF THE NEW PLANT

The present invention comprises a new and distinct cultivar of snapdragon, botanically known as *Antirrhinum hybrida*, and hereinafter referred to by the cultivar name 'Drayel'. The new cultivar is asexually reproduced from vegetative cuttings and tissue culture resulting from the cross of the seed/pod parent CF1-10, an unnamed and unpatented bronze proprietary line and the pollen parent CF1-105B, an unnamed and unpatented bronze proprietary line.

'Drayel' is a product of a planned breeding program intended to create new snapdragon cultivars with yellow colored flowers, dark green foliage, vigorous growth and basal branching.

The new cultivar was created in 1999 in Gilroy, Calif. and has been asexually reproduced repeatedly by vegetative cuttings and tissue culture in Gilroy, Calif. over a 1½ year period. It has also been trialed at Gilroy, Calif.; Litchfield, Mich. and Andijk, The Netherlands. It has been found to retain its distinctive characteristics through successive propagations; and this novelty is firmly fixed.

DESCRIPTION OF PHOTOGRAPH

This new snapdragon plant is illustrated by the accompanying photograph which shows blooms, buds, and foliage of the plant in full color, the colors shown being as true as can be reasonably obtained by conventional photographic procedures.

FIG. 1 shows the mature inflorescence.

DESCRIPTION OF THE NEW CULTIVAR

The following detailed descriptions set forth the distinctive characteristics of 'Drayel'. The data which defines these characteristics were collected from asexual reproductions by tissue culture/vegetative cuttings carried out in Gilroy, Calif. The plant history was taken on 19–21 week old plants grown in 8 inch pots, blossomed under natural light in a greenhouse and color readings were taken in the greenhouse in Gilroy, Calif. Color references are primarily to The R.H.S. Colour Chart of The Royal Horticultural Society of London (R.H.S.).

THE PLANT

Classification:
*Botanical.*—*Antirrhinum hybrida.*
*Commercial.*—Snapdragon.
Form: Low trailing annual, decumbent.
Growth and branching habit: Vigorous growing, basal branching.
Height:
*From soil level to top of plant.*—17–20 cm without racemes; 21–24 cm with racemes.
Width: 32–35 cm without racemes; 40–44 cm with racemes.
Time to produce a finished flowering plant: 12 weeks.
Outdoor plant performance: Semi-shade, suitable for containers or hanging baskets, as annuals.
Time to initiate roots: Approximately 9 days in the greenhouse.
Time to develop roots: Approximately 18 days in the greenhouse.
Root description: Fibrous, fleshy, white.

THE LEAVES

Arrangement: Opposite on stems and alternate on peduncles.
Length: 2.3–2.6 cm.
Width: 0.8–1.0 cm.
Leaf blade shape: Lanceolate/elliptic.
Leaf margin: Entire.
Apex aspect: Acute.
Base aspect: Cuneate.
Texture: Villous and glandular hairs.
Venation: Palmate, green RHS 144B.
Color:
*Upper side.*—Green RHS 137A.
*Under side.*—Green RHS 147B.
Petiole:
*Length.*—0.3 cm.
*Diameter.*—0.1 cm.
*Color.*—Green RHS 137A.
*Texture.*—Villous.

THE STEM

Length including peduncle: 17–20 cm.
Diameter: 2.0–3.0 cm.

Internode length: 1.3–1.5 cm.
Color: Green RHS 138B.
Texture: Villous.
Anthocyanin: None.

THE BUD

Shape: Obovate.
Diameter: 0.9–1.4 cm.
Length: 1.5–2.3 cm.
Color at tight bud: Light yellow RHS 3C.

THE FLOWER

Blooming habit: Continuous throughout the growing season.
Period of time to produce a flowering plant: 12 weeks in the greenhouse.
Inflorescence type: Terminal raceme.
Racemes per plant: 25–30 in the greenhouse.
Flowers per raceme: 4–11 in the greenhouse.
Peduncle:
*Length.*—11.8–14.0 cm.
*Diameter.*—0.1–0.2 cm.
*Color.*—Green RHS 138B.
*Texture.*—Pilose and glandular hairs.
Raceme:
*Length.*—6.9–7.5 cm.
*Diameter.*—0.1 cm.
*Texture.*—Pilose and glandular hairs.
Pedicel:
*Length.*—0.5 cm.
*Diameter.*—0.1 cm.
*Color.*—Green RHS 143C.
*Texture.*—Glandular hairs.
Flower:
*Form.*—Gametopetalous, bilabiate, upper lip erect with 2 broad lobes; lower lip with elevated palate and 3 lobes spreading.
*Size.*—Height 2.5–2.9 cm; Width 2.1–2.4 cm; Length 3.4–3.5 cm.
Lip color: Upper lip light yellow RHS 1A on outer ½ margin, white RHS 155D on basal ½ with red-purple RHS 59B vertical veining (both surfaces); Lower lip yellow RHS 2A (both surfaces).
Palate color: Yellow RHS 2A.
Throat color: Outside is white RHS 158D; Inside is white RHS 155D with red-purple RHS 59B veination, hairs yellow RHS 2A.
Outer throat texture: Pilose and glandular hairs.
Number of petals; Bilabiate.
Lip:
*Size.*—Upper lip size (2 lobes) 1.3–1.5 cm in length; 2.6–2.8 cm in width; Lower lip size (3 lobes) is 1.7–1.8 cm length; 2.3–2.5 cm in width.
*Margin: Entire.*
*Upper texture.*—Papillose.
Sepals: 5, not fused.
Sepal:
*Length.*—0.7 cm.
*Width.*—0.3 cm.
*Shape.*—Oblong; margin is entire.
*Apex.*—Acute; base: fused.
*Color.*—Green RHS 143C; for upper and lower surfaces.
*Texture.*—Glandular hairs.
Lastingness of individual blooms: 11–13 days in greenhouse environment.
Fragrance: None.

THE REPRODUCTIVE ORGANS

Stamens: 4, not fused; filament color with slight (2 mm) spot dark red RHS 59C and length 2 at 1.5 cm and 2 at 1.8 cm and yellow-white RHS 158D; 8 anthers yellow RHS 16C.
Pollen amount and color: Moderate, yellow RHS 13A.
Pistil: 1 slightly recurved at stigma 1.4–1.5 cm; style length is 1.2 cm; color is light yellow-green RHS 150D; stigma color is green RHS 149C.
Fruit seed set: Approximaitely 75 seeds/pod, 1 mm round, grey-purple RHS N186A.

DISEASE AND INSECT RESISTANCE

No susceptibility to diseases or insects noted to date.

COMPARISON WITH KNOWN CULTIVARS

When the instant plant is compared to Luminaire Yellow (not patented), the 'Drayel' foliage is lanceolate-elliptic while Luminaire Yellow is elliptic-ovate. Additionally 'Drayel' is a deeper yellow color than Luminaire Yellow. The base of the upper lip of 'Drayel' has light crimson bars, which are absent from Luminaire Yellow.

When the instant plant is compared to 'Draivory' (co-pending U.S. Plant patent application Ser. No. 10/059,105) the color of 'Drayel' is brighter yellow RHS 1A with palette RHS 2A and 59B veining on the upper lip. Draivory's color is much less intense. Draivory's upper lip color is RHS 11D and RHS 158D with veining of 70B. Lower lip color is RHS 4D and palette is 3A. 'Drayel' is a much more vigorous plant as well.

When the present invention is compared to parental cultivar CF1-10, Drayel has yellow colored flowers while CF1-10 has bronze flowers. Drayel is more branched at the base of the plant than CF1-10 and Drayel is earlier to flower than CF1-10. The Drayel is compared to the pollen parent CF1-05B, Drayel has yellow flowers while CF1-05B is bronze colored flowers. Drayel is earlier to flower than CF1-05B and Drayel has broader leaves than CF1-05B.

I claim:

1. A new and distinct snapdragon plant as shown and described herein.

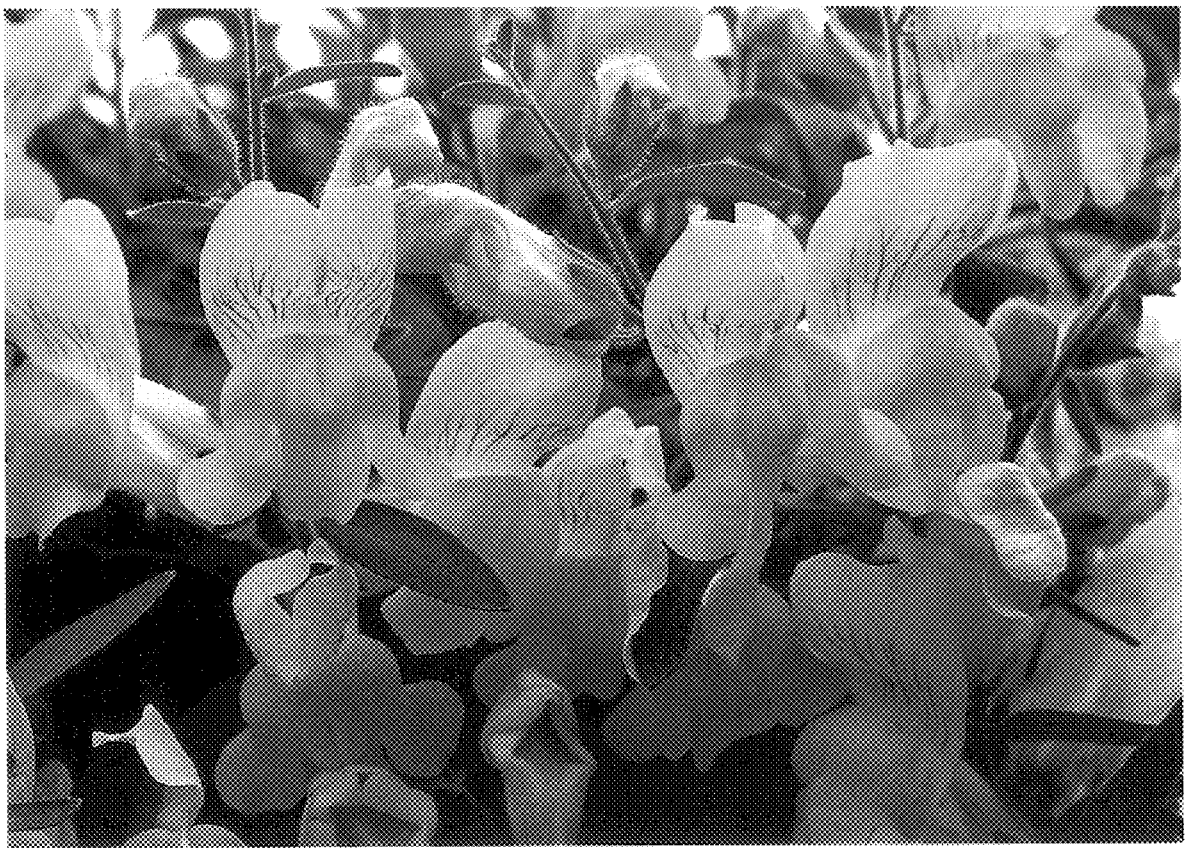

* * * * *